United States Patent [19]

Ku

[11] Patent Number: 5,474,554
[45] Date of Patent: Dec. 12, 1995

[54] METHOD FOR FIXATION OF AVULSION FRACTURE

[76] Inventor: Ming-Chou Ku, 13F-2, No. 1-28, Hsi Ping Nan Lane, Sec 3, Hsi Tun Load, Taichung City, Taiwan

[21] Appl. No.: 280,668

[22] Filed: Jul. 27, 1994

[51] Int. Cl.$^6$ .................................................. A61B 17/68
[52] U.S. Cl. ................... 606/72; 606/74; 606/86; 606/99; 606/104; 227/147
[58] Field of Search ................ 606/60, 74, 103, 606/72, 86, 99, 100, 104, 105, 224, 226, 232; 227/147

[56] References Cited

U.S. PATENT DOCUMENTS

| | | | |
|---|---|---|---|
| 2,411,079 | 11/1946 | Baule | 606/226 |
| 4,968,315 | 11/1990 | Gatturna | 606/232 |
| 5,123,584 | 6/1992 | Harrison | 227/147 |
| 5,141,520 | 8/1992 | Goble et al. | 606/232 |

Primary Examiner—Tamara L. Graysay
Attorney, Agent, or Firm—Bacon & Thomas

[57] ABSTRACT

A suture-wire device for fracture fixation is composed of a metal pin and a segment of wire. The anterior part of the device is a metal pin with sharp tip and a hole at the end where one segment or multiple segments of flexible wire is connected. The wire is embedded in the hole and tightly fixed by mechanical methods into one piece. An impactor is a metal cylinder with conical end having a trough which is slightly wider than the diameter of wire along the core of the impactor. After reduction of the fracture, two suture-wires are drilled across the fracture line in parallel. The impactor is applied onto a blunt end of the pin with the wire in the trough. The remaining part of the pins are then hammered into the bone by applying a force to the impactor. One of the wires of the two suture-wires is then bent and looped behind the tips of the pins which protrude from the other end of fractured bone. The two wires are then brought together and tightened, and the protruding ends of the pins are cut.

1 Claim, 3 Drawing Sheets

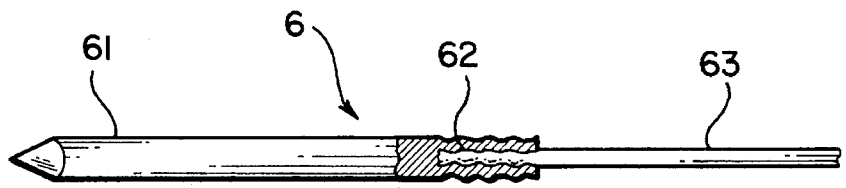
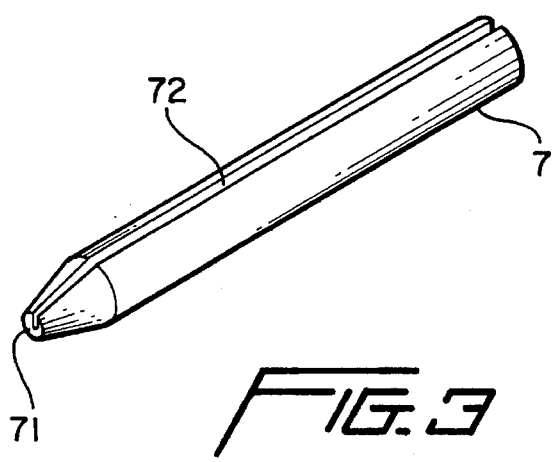
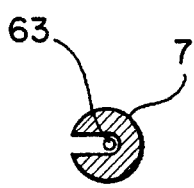
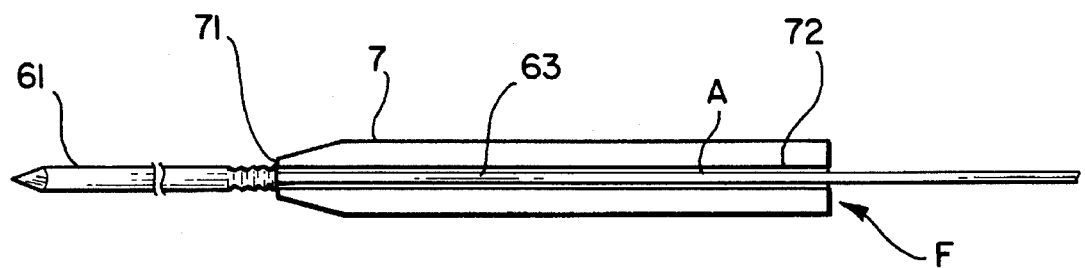

5,474,554

METHOD FOR FIXATION OF AVULSION FRACTURE

BACKGROUND OF THE INVENTION

1. Field of the Invention

The suture-wire fixation device is a new type of orthopaedic implant for fracture fixation. It is specially devised for avulsion fractures such as patella, olecranon, and malleolus. It is composed of a suture-wire and an impactor. The front part is a metal pin and the rear part is one or multiple segments of flexible wire. After reduction of the fracture, the pin is drilled into the bone across the fracture line with the tip coming out from the other end of bone. The impactor is seated onto the end of the pin with the wire within the trough of the impactor. The pin is hammered into the bone totally. With two pins passed through the fractured bone in parallel, one of the wires is bent and looped behind two protruding tips of the pins and is tightened to the other wire by twisting of the wires. The prominent pin tips are then cut. By doing so, the fracture is tightened and will not be pulled apart by muscle forces. Compared to the ordinary way of tension band wiring of fractures, this implant causes little irritation to the soft tissue and skin, and little migration is possible. Migration may impinge onto surrounding tissues and prevent the patient from early rehabilitation and recovery. Migration is also the cause of loss of fixation which may dictate another surgery. With this device, the operation time is shortened, because there is no need for bending of the wire ends which is sometimes time consuming. In conclusion, the method of fracture fixation with the suture-wire device is a good, safe and time efficient procedure which facilitates early recovery after surgery.

2. Description of the Prior Art

For a fractured bone, generally, the method of treatment includes internal fixation with implants such as a nail, plate, screw, pin and wire to hold the bone together while it heals. For the treatment of avulsion fractures such as patella, olecranon and malleolus, the most popular method nowadays is the tension band wiring technique recommended by ASIF (Association for Study of Internal Fixation). The technique uses two Kirschner wires which pass in parallel across the fracture line, and a segment of metal wire is looped around both ends of the Kirschner wires and tightened. The wire works as a tension band which holds the fracture fragments together and compresses the fragments during physiological loading of the bone. To explain the tension band wiring technique, illustrations of the procedure for fixation of a patellar fracture is shown as below (see FIGS. 1 a–1f):

Step A: With powered drill 1, two parallel drill holes are made over the fracture end 21 of the proximal fragment 2. Once the first hole is drilled, the drill is replaced with a smaller Kirschner wire, the wire then serves as a guide for the second drill hole.

Step B: Replace the Kirschner wires with 2 mm drill bits 11 inserted in proximodistal direction. Reduce the fracture fragments 2 and 2' with a pointed end reduction forceps 5.

Step C: If reduction is perfect, drill with the 2 mm drill bits the holes in the distal fragment 2'.

Step D: Replace drill bits by Kirschner wires 3 and 3', bent 180 degrees at proximal end into hooks 31 and 31'.

Step E: Secure the wire 4 over both ends of Kirschner wires and tighten with a wire tightener. Hammer the Kirschner wires over the wire 4 with bent ends 31 and 31' into the bone.

Step F: Cut the distal ends of both Kirschner wires 32 and 32', and the fixation is completed.

It is generally accepted that the tension bend wiring technique is effective in the fixation of a patella fracture, but some shortcomings do exist. First, the Kirschner wire is a smooth pin and may migrate during postoperative rehabilitation. The bent ends 31 and 31' are parallel to the smooth pin and frequently do not stop the migration. The sites of the fracture for application of tension bend wiring are usually superficial. Migrated Kirschner wires irritate the surrounding soft tissue and skin, produce pain and prevent the patient from early rehabilitation which is so important for an intra-articular fracture. Sometimes the wire may penetrate the skin and causes a pin tract infection. To bend the end of a Kirschner wire during operation takes time and some effort, and a perfect bend of 180 degree is not always possible. The imperfectly bent end may rotate and the wire may slip over the tip which results in loss of fixation and reduction. If the fracture fragment is small, the bending maneuver may break the bone into small pieces.

SUMMARY OF THE INVENTION

The purpose of this new design is to circumvent the pitfalls in the traditional way of fracture fixation. It can be used in almost all avulsion fractures including patella, olecranon of ulna, malleolus of tibia, and greater trochanter of femur (especially after osteotomy), etc. The anterior part of the suture-wire device is a smooth pin, at the end of it, a segment of flexible wires is embedded. After drilling into the bone, the end of the pin is totally impacted into the bone. After looping around the tips of two parallel pins, the flexible wires are tightened together to achieve a secure fixation of the fracture. There is no nuisance of bending the wire during the operation, and time is saved. The most important benefit of this new method is that there is no migration of the smooth pin if the pin is impacted into the bone. The pin and wire are in one piece and are not separable under usual circumstances. The device is safe, because there is no risk of vital organ damage from migration, and no skin irritation or pin tract infection as well.

The purpose of the invention is fulfilled through the following technical points:

A suture-wire device for fracture fixation includes a metal pin and wire, the anterior part is a rigid metal pin, at the end of which is a hole, the posterior part is a segment of flexible wire embedded in the hole on the pin and fixed into one piece by mechanical means such as pressing, or the like.

An impactor, a metal rod with a tapered tip, has a trough which is slightly wider than the diameter of the flexible wire along the center of the rod from the tapered tip to the end. By holding the end of the pin, the pin is drilled into the bone, the anterior part of the wire is snapped into the trough of the tapered end of the impactor. The pin is hammered into the bone. By looping around the tips of two parallel pins or through a hole over the distal fragment of the fractured bone, the wires are tightened and secure fixation is achieved. Since the end of the pin is buried in the bone by impaction, no irritation of the soft tissue and skin is possible. Because the pin and wire are in one piece, no migration of the pin is possible because of the tightened wire. Since no intra-operative bending of the pin is necessary, time may be saved.

From a technical point of view, the new design has apparent merits compared to the ordinary way of fixation in avulsion fracture such as patella, olecranon, malleolus, etc.

BRIEF DESCRIPTION OF THE DRAWINGS

The structure of the suture-wire will be shown in the diagram below.

FIG. 2 is a cross-section view of the suture-wire according to the present invention.

FIG. 3 is a perspective view of the impactor of the present invention.

FIG. 4 is a diagrammatic view showing how the suture-wire fits into the trough on the impactor.

FIG. 5 is a cross-sectional view of the structure in FIG. 4.

DETAILED DESCRIPTION OF THE PREFERRED EMBODIMENT

Figure 1A:
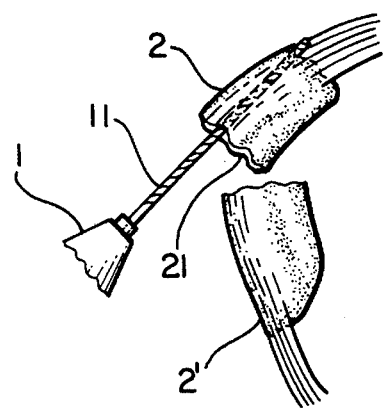
FIGS. 1a–1f are diagrams illustrating the ordinary method of tension band fixation for the patella recommended by ASIF.
Figure 1D:
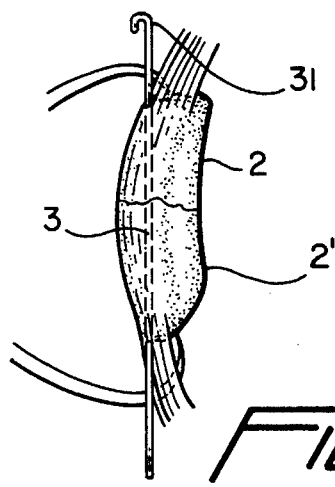
Figure 1B:
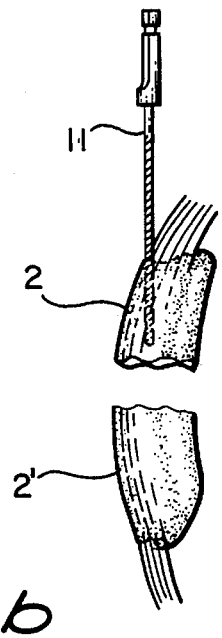
Figure 1E:
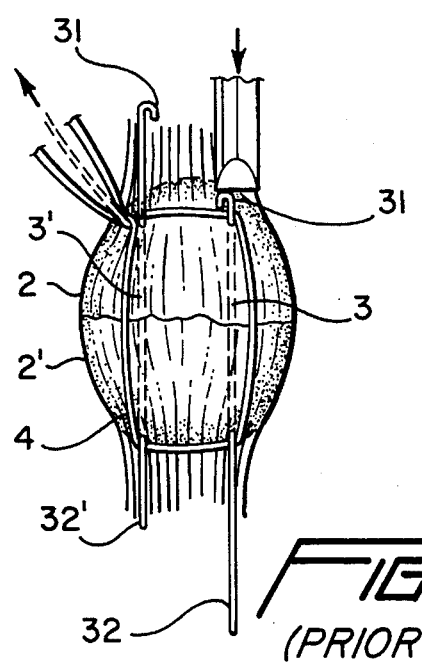
Figure 1C:
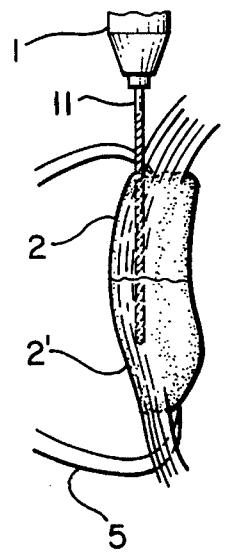
Figure 1F:
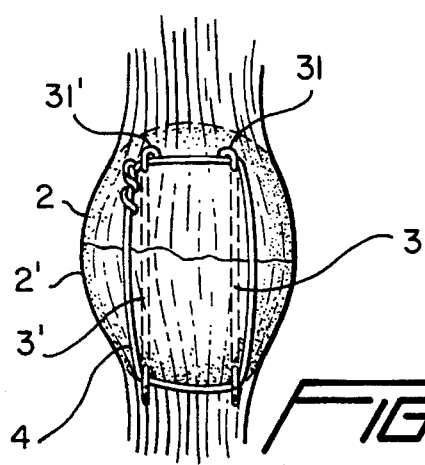
Figure 6A:
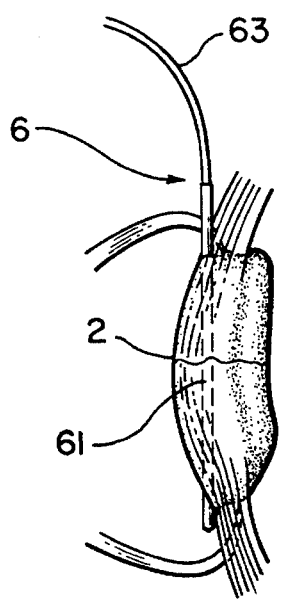
FIGS. 6a–6c illustrate the new method with suture-wire in the fixation of a patellar fracture.
Figure 6B:
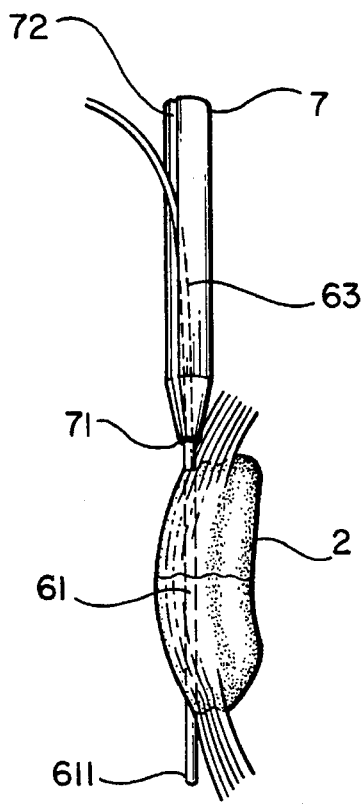
Figure 6C:
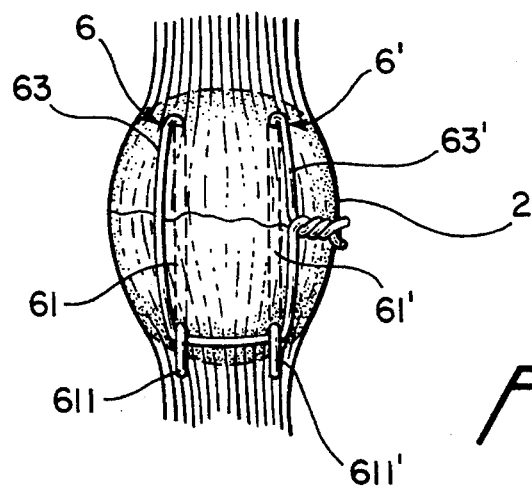

To show the structural characteristics and advantages of the new device, an explanation with diagram and surgical procedure on patellar fracture as an example is given as below:

First of all, referring to FIGS. 2 and 3, the suture-wire device for fracture fixation is mainly designed for avulsion fractures, such as patella, olecranon and malleolus of tibia and fibula. It is composed of suture-wire 6, and impactor 7. The impactor is the tool used to hammer the pin part of the suture-wire into the bone. The anterior part of the suture-wire is a rigid metal pin 61, on the end of the pin there is a hole 62. The rear part of the device is a segment (may be multiple segments) of flexible wire 63. The wire 63 is embedded in the hole 62 on the pin 61 by a known mechanical method with secure connection. The front part of the impactor 7 is conical with blunt tip 71. From the conical end 71 to the opposite end, along the center of the cylindrical rod, there is a trough 72 which is slightly wider than the diameter of the wire 63. On the fixation of a fractured patella with the suture-wire device, the surgical procedure is shown in FIG. 6:

Step A': After reduction of the fracture, two parallel suture-wires 6 and 6' are drilled through the bone 2 proximodistally until the drill is close to the bone.

Step B': The wire part of the suture-wire 63 is snapped into the trough 72 on the impactor 7 and the impactor is moved along the wire down to the pin, as shown in FIGS. 4 and 5. The wire is bent at the middle part of the impactor A to keep the end of the impactor free of wire and ready for hammering. The pin is then hammered into the bone by external force F on the end of the impactor 7.

Step C': The wire 63 at the end of the pin 61 is bent and passed behind the tips 611 and 611' of the pins 61 and 61' which are protruding at the other end of the fracture bone, and is then brought to the wire 63' of the parallel pin and tightened. The tips 611 and 611' of pins 61 and 61' are then cut short.

From the illustration of the structure and description of the surgical procedure, two advantages of the new device are evident. First, no migration of the pin is possible as long as the suture-wire is intact, because the pin and wire are a single piece. The connection is mechanically sound under mechanical tests as well as in clinical trials. There is no irritation of soft tissue and skin, and no risk to nearby vital organs. Second, there is no fuss with bending of the tips of Kirschner wires during the operation, which is not always trouble-free. In case of inadequate bending and impaction of the end of the Kirschner wire into the bone, the known pin may turn around allowing dislodgement of the wire over the end of the pin which may result in loss of fixation. No such thing is possible in the new device. Time may be saved since bending of the wire end is unnecessary.

I claim:

1. A method for fixation of an avulsion fracture having at least two bone sections with the fracture located between the bone sections, comprising the steps of:

a) providing two suture wire fixation devices, each comprising:

i) an implant portion comprising an elongated, substantially cylindrical pin configured to pass through the at least two bone sections across the fracture such that at least a first end, of the pin extends externally of the bone sections and having a second end and at least one elongated flexible wire fixedly attached to the second end of the pin; and, ii) an impactor having a generally cylindrical configuration with a first, tapered end, a second, opposite end and provided with a trough extending along the length of the impactor which opens through an external side surface of the impactor and the first and second ends, wherein the width of the trough is greater than the width of the at least one elongated flexible wire, the impactor located such that the first, tapered end bears against the second end of the pin and a portion of the elongated flexible wire is located in the trough, whereby a force exerted on the second end of the impactor urges the pin into the bone sections.

b) reducing the fractured bone by placing the at least two bone sections together at the fracture;

c) placing the pins into the bone sections;

d) exerting a force on the second end of the impactors so as to drive the pins through the at least two bone sections such that the pins extend across the fracture, oriented generally parallel to each other and the first ends of the pins extend exteriorly of the at least two bone sections;

e) passing the elongated, flexible wire from one suture wire fixation device between a bone section and the exterior first end portions of both suture wire fixation devices; and f) fastening the elongated, flexible wires of both suture wire fixation devices together.

* * * * *